US00PP36400P2

(12) United States Plant Patent
Koot

(10) Patent No.: US PP36,400 P2
(45) Date of Patent: Jan. 14, 2025

(54) ***COLEUS* PLANT NAMED 'Docoldotonas'**

(50) Latin Name: *Coleus scutellarioides*
Varietal Denomination: Docoldotonas

(71) Applicant: DUMMEN GROUP B.V., De Lier (NL)

(72) Inventor: Arjan Koot, Oeffelt (NL)

(73) Assignee: DÜMMEN GROUP B.V., De Lier (NL)

( * ) Notice: Subject to any disclaimer, the term of this patent is extended or adjusted under 35 U.S.C. 154(b) by 0 days.

(21) Appl. No.: 18/444,739

(22) Filed: Feb. 18, 2024

(51) Int. Cl.
*A01H 6/00* (2018.01)
*A01H 5/12* (2018.01)

(52) U.S. Cl.
USPC ..... Plt./469

(58) Field of Classification Search
USPC ..... Plt./469
CPC ..... A01H 6/00; A01H 5/12
See application file for complete search history.

*Primary Examiner* — Keith O. Robinson
(74) *Attorney, Agent, or Firm* — C. Anne Whealy

(57) ABSTRACT

A new and distinct cultivar of *Coleus* plant named 'Docoldotonas', characterized by its compact, upright to somewhat outwardly spreading plant habit; vigorous growth habit and rapid growth rate; freely branching habit; relatively small variegated leaves with brown-colored centers and yellowish green-colored margins; and good garden performance.

1 Drawing Sheet

Botanical designation: *Coleus scutellarioides*.
Cultivar denomination: 'DOCOLDOTONAS'.

STATEMENT REGARDING PRIOR DISCLOSURES BY INVENTOR AND APPLICANT/ASSIGNEE

An European Community Plant Breeder's Rights application for the instant plant was filed by the Applicant/Assignee, Dümmen Group B.V. of De Lier, The Netherlands on Sep. 28, 2023, application number 2023/2029. Foreign priority is not claimed to this application.

The Inventor and Applicant/Assignee assert that no sales, offers for sale or public distribution of the instant plant occurred more than one year prior to the effective filing date of this application.

Any information about the claimed plant would have been obtained from a direct or indirect disclosure from the Inventor and/or Applicant/Assignee. Inventor and Applicant/Assignee claim a prior art exception under 35 U.S.C. 102(b)(1) for disclosures and/or sales prior to the filing date but less than one year prior to the effective filing date.

BACKGROUND OF THE INVENTION

The present invention relates to a new and distinct cultivar of *Coleus* plant, botanically known as *Coleus scutellarioides* and hereinafter referred to by the name 'Docoldotonas'.

The new *Coleus* plant is a product of a planned breeding program conducted by the Inventor in Rheinberg, Germany. The objective of the breeding program was to develop new compact and freely branching *Coleus* plants with strong branches and attractive foliage.

The new *Coleus* plant originated from a cross-pollination in July 2021 of a proprietary selection of *Coleus scutellarioides* identified as code number CS-0394, not patented, as the female, or seed, parent with a proprietary selection of *Coleus scutellarioides* identified as code number CS-0242, not patented, as the male or pollen, parent. The new *Coleus* plant was discovered and selected by the Inventor as a single flowering plant from within the progeny of the stated cross-pollination in a controlled greenhouse environment in Rheinberg, Germany in April 2022.

Asexual reproduction of the new *Coleus* plant by vegetative tip cuttings in a controlled greenhouse environment in Rheinberg, Germany since May 2022 has shown that the unique features of this new *Coleus*plant are stable and reproduced true to type in successive generations.

SUMMARY OF THE INVENTION

The new *Coleus* plant has not been observed under all possible combinations of cultural practices and environmental conditions. The phenotype may vary somewhat with variations in environment and cultural practices such as temperature and light intensity without, however, any variance in genotype.

The following traits have been repeatedly observed and are determined to be the unique characteristics of 'Docoldotonas'. These characteristics in combination distinguish 'Docoldotonas' as a new and distinct *Coleus* plant:

1. Compact, upright to somewhat outwardly spreading plant habit.
2. Vigorous growth habit and rapid growth rate.
3. Freely branching habit.
4. Relatively small variegated leaves with brown-colored centers and yellowish green-colored margins.
5. Good garden performance.

Plants of the new *Coleus* differ primarily from plants of the female parent selection in the following characteristics:

1. Plants of the new *Coleus* are more compact than and not as vigorous as plants of the female parent selection.
2. Leaves of plants of the new *Coleus* have brown-colored centers and yellowish green-colored margins whereas leaves of plants of the female parent selection are green in color with yellow-colored centers.

Plants of the new *Coleus* differ primarily from plants of the male parent selection in the following characteristics:

1. Plants of the new *Coleus* are more compact than and not as vigorous as plants of the male parent selection.
2. Plants of the new *Coleus* have smaller leaves than plants of the male parent selection.
3. Leaves of plants of the new *Coleus* have brown-colored centers and yellowish green-colored margins whereas leaves of plants of the male parent selection are solid green in color.

Plants of the new *Coleus* can be compared to plants of *Coleus scutellarioides* 'Stained Glassworks® Le Freak', not patented. In side-by-side comparisons plants of the new *Coleus* differ from plants of 'Stained Glassworks® Le Freak' in the following characteristics:

1. Plants of the new *Coleus* are more compact than and not as vigorous as plants of 'Stained Glassworks® Le Freak'.
2. Plants of the new *Coleus* have smaller leaves than plants of 'Stained Glassworks® Le Freak'.
3. Leaves of plants of the new *Coleus* have uniformly serrate margins whereas leaves of plants of 'Stained Glassworks® Le Freak' have entire or randomly serrated margins.
4. Leaves of plants of the new *Coleus* have brown-colored centers and yellowish green-colored margins whereas leaves of plants of 'Stained Glassworks® Le Freak' have dark red-colored centers and light yellowish green-colored margins.

BRIEF DESCRIPTION OF THE PHOTOGRAPH

The accompanying colored photograph illustrates the overall appearance of the new *Coleus* showing the colors as true as it is reasonably possible to obtain in colored reproductions of this type. Colors in the photograph may differ slightly from the color values cited in the detailed botanical description which accurately describe the colors of the new *Coleus*.

The photograph is a side perspective view of a typical plant of 'Docoldotonas' grown in a container.

DETAILED BOTANICAL DESCRIPTION

The aforementioned photograph and following observations, measurements and values describe plants grown in Rheinberg, Germany in 22-cm containers in a glass-covered greenhouse during the spring and early summer and under cultural practices which closely approximate commercial *Coleus* production. During the production of the plants, day and night temperatures averaged 18° C. and light levels averaged from 4,500 lux. Plants were pinched one time three weeks after planting rooted cuttings. Plants were twelve weeks old when the photograph was taken and 25 weeks old when the description was taken. In the following detailed description, color references are made to The Royal Horticultural Society Colour Chart, Fifth Edition, except where general terms of ordinary dictionary significance are used.

Botanical classification: *Coleus scutellarioides* 'Docoldotonas'.

Parentage:

*Female, or seed, parent*.—Proprietary selection of *Coleus scutellarioides* identified as code designation CS-0394, not patented.

*Male, or pollen, parent*.—Proprietary selection of *Coleus scutellarioides* identified as code number CS-0242, not patented.

Propagation:

*Type*.—By vegetative cuttings.

*Time to initiate roots, summer*.—About five days at temperatures about 20° C.

*Time to initiate roots, winter*.—About seven days at temperatures about 20° C.

*Time to produce a rooted young plant, summer*.—About three weeks at temperatures about 20° C.

*Time to produce a rooted young plant, winter*.—About four weeks at temperatures about 20° C.

*Root description*.—Fine, fibrous; typically white in color, actual color of the roots is dependent on substrate composition, water quality, fertilizers, substrate temperature and age of roots.

*Rooting habit*.—Freely branching; dense.

Plant description:

*Plant and growth habit*.—Compact, upright to outwardly spreading plant habit; vigorous growth habit and rapid growth rate; freely branching habit with about seven primary lateral branches each with about four secondary lateral branches developing per plant.

*Plant height*.—About 21.5 cm.

*Plant diameter*.—About 59.25 cm.

Lateral branch description:

*Length*.—About 25.5 cm.

*Diameter*.—About 8 mm.

*Internode length*.—About 3.1 cm.

*Strength*.—Moderately strong; flexible.

*Aspect*.—Mostly upright.

*Texture and luster*.—Pubescent; semi-glossy.

*Color, when developing*.—Close to 144A.

*Color, fully developed*.—Close to 143C.

Leaf description:

*Arrangement*.—Decussate, simple.

*Length*.—About 5 cm.

*Width*.—About 1.95 cm.

*Shape*.—Elliptic.

*Apex*.—Caudate.

*Base*.—Attenuate.

*Margin*.—Serrate; sinuses medium in depth and divergent.

*Texture and luster, upper surface*.—Slightly pubescent, not rugose; velvety; matte.

*Texture and luster, lower surface*.—Glabrous, rugose; matte.

*Venation pattern*.—Pinnate.

*Color*.—Developing leaves, upper surface: Centers, close to N144C and towards the margins, close to 177B. Developing leaves, lower surface: Close to N144D. Fully expanded leaves, upper surface: Centers, close to N199B and towards the margins, close to 144A; venation, close to 186A and 187A. Fully expanded leaves, lower surface: Close to 144B; venation, close to 144A.

*Petioles*.—Length: About 1.7 cm. Diameter: About 1.1 mm. Strength: Moderately strong to weak. Texture and luster: Slightly pubescent; semi-glossy. Color, upper and lower surfaces: Close to 145A.

Flower description: To date, flower development has not been observed on plants of the new *Coleus*.

Pathogen & pest resistance: To date, plants of the new *Coleus* have not been observed to be resistant to pests and pathogens common to *Coleus* plants.

Garden performance & temperature tolerance: Plants of the new *Coleus* have been observed to have good garden performance and to tolerate temperatures ranging from 5° C. to 40° C.

It is claimed:

1. A new and distinct *Coleus* plant named 'Docoldotonas' as illustrated and described.

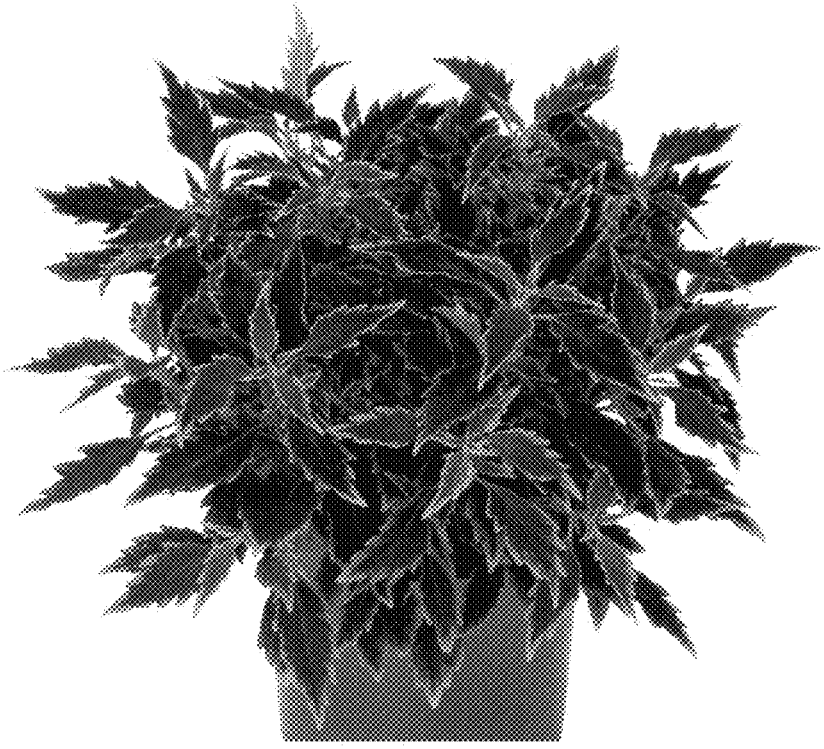

* * * * *